United States Patent [19]

Dickhudt

[11] 4,411,277
[45] Oct. 25, 1983

[54] IMPLANTABLE CONNECTOR

[75] Inventor: Eugene A. Dickhudt, New Brighton, Minn.

[73] Assignee: Medtronic, Inc., Minneapolis, Minn.

[21] Appl. No.: 258,260

[22] Filed: Apr. 28, 1981

[51] Int. Cl.³ ............................................. A61N 1/04
[52] U.S. Cl. .................................................. 128/784
[58] Field of Search ............. 128/419 P, 784; 339/60, 339/61, 75 R, 75 M, 256 S, 119 R, 120, 122 F, 125, 252 P, 259 R; 46/1 R; 24/115 N

[56] References Cited

U.S. PATENT DOCUMENTS

| | | | |
|---|---|---|---|
| 869,686 | 10/1907 | Bauno | 46/1 R |
| 983,258 | 1/1911 | Bliss | 339/75 M |
| 1,657,253 | 1/1928 | Fortin | 339/256 S |
| 2,183,067 | 12/1939 | Gardner | 339/252 P |
| 2,393,083 | 1/1946 | Wisegarver | 339/256 S |
| 2,427,001 | 9/1947 | Hubbell et al. | 339/256 S |
| 2,711,331 | 6/1955 | Temple | 24/115 N |
| 2,840,676 | 6/1958 | King | 339/60 R |
| 3,058,083 | 10/1962 | Schneider | 339/256 S |
| 3,124,405 | 3/1964 | Massa | 339/75 M |
| 3,253,595 | 5/1966 | Murphy et al. | 128/405 |
| 3,440,333 | 4/1969 | Blomstrand | 339/256 S |
| 3,760,332 | 9/1973 | Berkovits | 339/66 R |
| 3,924,921 | 12/1975 | Feightner | 339/252 P |
| 4,112,953 | 9/1978 | Shanker | 128/419 |
| 4,142,532 | 3/1979 | Ware | 128/419 |
| 4,236,525 | 12/1980 | Sluetz et al. | 128/419 |
| 4,332,259 | 6/1982 | McCorkle, Jr. | 128/786 |

FOREIGN PATENT DOCUMENTS 821722  5/1937  France ............................. 339/259 R Primary Examiner—William E. Kamm
Assistant Examiner—Mitchell J. Shein
Attorney, Agent, or Firm—Robert J. Klepinski; John L. Rooney; Joseph F. Breimayer

[57] ABSTRACT

A body implantable connector for connecting to an implantable device, such as an electrical lead. The connector has a sheath for frictionally fitting over the end of the lead, the sheath being of a pliant material of sufficient strength to resist breaking under the forces normally exerted on the connector, but sufficiently pliable to deform under the frictional forces created between the sheath and lead when they are urged in opposite directions, so that when a force is exerted to pull the sheath from the lead it will stretch causing its diameter to decrease and grip the lead more tightly. In one embodiment a wire extends longitudinally within the sheath and mates with a lumen in the conductor of the lead to make electrical connection to the lead. A means for compressing the sheath about the lead, such as a suture or O-ring, may be used to further secure the sheath to the lead.

8 Claims, 4 Drawing Figures

IMPLANTABLE CONNECTOR

BACKGROUND OF THE INVENTION

1. Field of the Invention

The invention in general relates to the field of implantable connectors for making physical and electrical connection to an implantable lead and, more particularly, concerns an improved connector with a dynamic gripping action that permits a positive connection without the use of set screws, adhesives, etc.

2. Description of the Prior Art

In recent years many devices have been developed which are designed for implantation in a body. For example, electrical tissue stimulators are now routinely implanted in humans for treatment of heart block, pain, scoliosis, and other medical problems. Generally an electrical lead is used with these devices to carry an electrical current or voltage from a pulse generator or other electrical device to the body part that needs to be treated. Such leads generally consist of a conductor encased in an insulator which is generally inert to body fluids. In many such leads the conductor is in the form of a coil, with a passage down the center of the coil called a lumen. In some cases, it is necessary that several different types of the leads need to be used in order to effectively deliver the electrical voltage or current to the appropriate portion of the body. For example, when stimulating the spinal cord it is necessary to use a very thin lead over the portion of the conductive path which passes through the epidural space, while in the portion of the electrical path which passes through muscle and surface tissue it is desirable to use a lead that is thicker and stronger and thus more resistant to breakage. Connectors are generally used to make the physical and electrical connection between the two portions of the lead in such a situation. Connectors are also used in connecting the lead to the terminal of the electrical device which produces the current or voltage.

Conventional electrical connectors used in external applications generally are not suitable for use with implanted devices. Implanted devices must be highly reliable because patients' health and life may depend on them for long periods, such as ten years or more, and because they cannot be replaced except by expensive and traumatic surgical procedures. In addition, such devices must be capable of such high reliability in a hostile environment—the human body—in which they are subject to much movement and flexing. For these reasons, up to now, such connectors have consisted of relatively complex positive fixation devices encased in protective materials. Perhaps most common of such devices has been a pin and socket-type arrangement containing a set screw in the socket which can be screwed down upon the pin after the pin is inserted to positively hold the pin in place, with the whole encased in protective medical-grade silicone or similar material. Such connectors tend to be significantly larger than the lead itself and thus add significant bulk to the implantable lead. The larger the implanted device the more trauma it may cause to the body and, thus it is desirable to have smaller connectors. One solution to this problem has been the use of medical adhesive to hold a pin and socket device together. While the use of the medical adhesive may solve some of the bulk problem it has its own disadvantages, such as difficulty in making a disconnection without destroying the part if a disconnection is necessary, contamination of the site due to particles which may become loose, failure of the adhesive under flexing, etc.

Conventional implantable electrical connectors have up to now required special fittings on the lead or other terminal which is to be connected to, in order to ensure a positive fixation. Thus leads must be specially made in fixed lengths with the fittings attached. Since human bodies are of various sizes this results in the necessity of stocking many different lengths of leads, which is expensive and impractical, or the implanting of leads that are longer than necessary and the coiling of the excess length within the body. The excess length adds further bulk to the implanted material and provides additional opportunities for failure and trauma due to the presence and flexing of the superfluous lead length.

SUMMARY OF THE INVENTION

It is an object of the invention to provide an implantable connector which is simple and relatively small compared to prior art connectors, and which avoids one or more of the above-stated disadvantages of the prior art connectors.

The invention provides a body implantable connector for connecting to a terminal of the type having a conductor, and preferably the terminal being the end of a lead having a coiled electrical conductor having a central lumen, the conductor being encased in an insulator which is generally inert to body fluids. The invention includes in combination, a means for making conductive connection to the terminal conductor and a sheath means for frictionally fitting about the terminal. The sheath means is of a pliant material having sufficient strength to resist breaking under the forces normally exerted on the connector, but sufficiently pliable to deform and contract about the terminal under the frictional forces created between the sheath means and the terminal when they are urged in a direction tending to separate them. The pliable material is composed of material which is generally inert to body fluids.

The positive fixation of the sheath to the terminal, such as a lead, is derived from the fact that forces tending to pull the lead from the sheath will cause the sheath to stretch whereupon its interior dimension will decrease, causing it to more firmly grip the lead. The greater the forces tending to pull the sheath from the lead the greater will be the stretch and the more the grip will increase. Thus the sheath dynamically reacts to provide increased holding force exactly when it is needed, that is, when forces are placed on the lead and connector tending to separate them. Since the lead will stretch under the forces created between the sheath and the lead which, in turn, contracts the sheath and causes the gripping strength to increase, the pliable material will break before the grip is released. Thus, providing that the pliable material is of sufficient strength to resist breaking under the normal forces exerted on the connector, the connector and the lead will remain connected under any such forces.

Preferably the means for making conductive connection to the conductor is a wire which mates within the lumen of the conductor. Preferably there is a bent portion of the wire which projects a radical distance from the axis of the unbent portion of the wire which is greater than the radius of wire, which electrically contacts the interior of the lead coil.

In one aspect the invention provides an implantable connector in which the portion which serves to protect the electrical connection also serves to provide a means of positive fixation between the connector and the lead.

A means for further compressing the sheath means about the lead, such as a suture or an O-ring may be included in order to further secure the sheath about the lead. Preferably, in the embodiment including the O-ring, there is a means attached to the sheath for supporting the O-ring in a stretched condition out of contact with the sheath means, so that the lead may be inserted into the sheath means without interference from the O-ring. Preferably, there is also a means for hindering the O-ring from slipping off the end of the sheath means.

The invention also contemplates a new method of connecting to an implantable lead, including the steps of severing the lead at the point where it is desired to make the connection and inserting the severed end into the connector to make physical and electrical connection between the lead and the connector.

Numerous other features, objects and advantages of the invention will become apparent from the following detailed description when read in conjunction with the accompanying drawings.

DESCRIPTION OF THE PREFERRED EMBODIMENT

Figure 1:
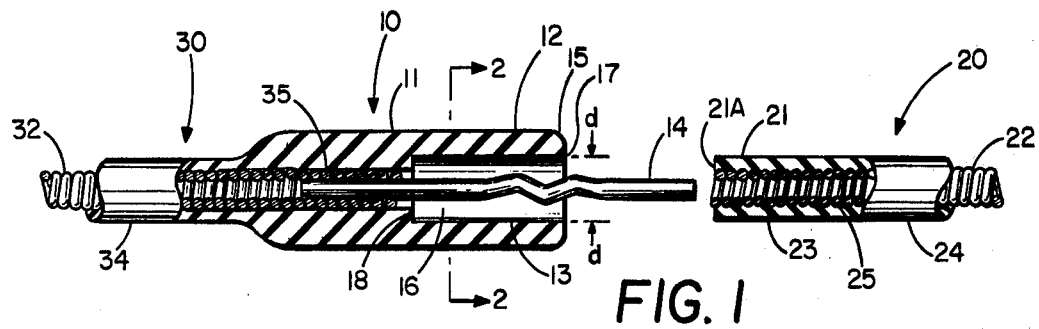
FIG. 1 is a partially cutaway view of a connector according to the invention in an embodiment in which the connector is integrally formed at the end of one lead, and showing the connector in position to be connected to the end of a second lead also shown in the view.
Figure 3:
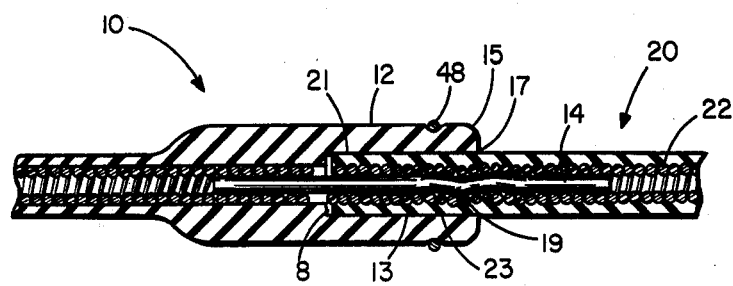
FIG. 3 is a sectional view of the connector and leads of FIG. 1 taken longitudinally through the axis of the connector and leads, showing the end of the second lead inserted into the connector and with a suture tied about the connector.

Directing attention to FIG. 1, a connector 10, according to one embodiment of the invention, is shown in a position about to be connected to terminal 21, which in this case is an end portion 21 to a lead 20. In FIG. 3, connector 10 is shown connected to lead 20, the end 21 of lead 20 having been placed within sheath means 12 of connector 10 and electrical connection means 14 of connector 10 having made electrical contact with the interior of conductor 22. The inner diameter of sheath 12, shown as d—d in FIG. 1, is less than or equal to the external diameter of lead end 21 so that inner surface 13 of sheath 12 frictionally contacts the outer surface 23 of lead end 21. Sheath means 10 is made of a pliant material having sufficient strength to resist breaking under the force normally exerted on the connector 10, but sufficiently pliable to deform and contract about lead end 21 under the frictional forces created between the surfaces 13 and 23 when sheath 10 and lead end 21 are urged in opposing directions. Thus, if forces are exerted for example to pull sheath 10 to the left (FIG. 3) and lead 20 to the right, the frictional force between the surfaces 13 and 23 will cause sheath 12 to stretch. The stretching of sheath 12 causes the diameter d—d to contract, further increasing the frictional forces between surfaces 13 and 23 sufficiently to prevent the lead 20 from slipping out of connector 10.

Proceeding now with a detailed description of the various embodiments of the invention, FIG. 1 shows an embodiment of the invention in which the connector 10, according to invention, is employed in making the connection between a lead 30 and the end of a second lead 20. Connector 10 is intricately formed as the end portion of lead 30. Lead 30 comprises a coil conductor 32 encased in an insulator 34. Connector 10 comprises sheath 12 having a cylindrically shaped hollow passage 16 opening at end 17. Sheath 12 is preferably integrally molded with insulator 34 so that they form one continuous piece. Coil conductor 32 extends substantially to a closed end 18 of hollow cylinder 16. Connector 10 also includes means 14 for making electrical connection to conductor 22 of lead 20. Means 14 comprises a length of wire 14 extending a short distance into coil 32 and attached to coil 32 by means of a weld 35. Wire 14 is bent to form several projections 19, which extend a distance greater from the axis of wire 14 than the radius of wire 14. Conductor 22 of lead 20 is a coil conductor having a void central portion 25 which is conventionally referred to as a lumen. Wire 14 has a diameter less than or equal to diameter of lumen 25. Wire 14 extends substantially longitudinally within sheath 12, that is, substantially along a direction parallel to the axis of sheath 12, and is preferably attached to sheath 12; in the embodiment shown the attachment is by means of attachment to coil 35 which is embedded in closed end 11 of sheath 12. "Substantially" here means near enough to a longitudinal direction that it will not block the interior passage 16 of sheath 12 preventing lead 20 from entering the passage 16. For example, the invention contemplates an embodiment in which wire 14 does not have bends such as 19 but is inclined slightly to the axis of sheath 12 so that it will contact the interior of coil 22 sufficiently to make good electrical contact, but not so much as to impede the slipping of lead end 21 into sheath 12.

Figure 2:
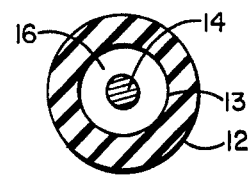
FIG. 2 is cross sectional view of the connector of FIG. 1 taken through line 2—2 of FIG. 1.

FIG. 2 shows a sectional view of the connector of FIG. 1 taken through lines 2—2 of FIG. 1. This view more clearly shows the cylindrical shapes of sheath 12; passage 16 and wire 14 in this embodiment.

FIG. 3 shows the connector 10 of FIG. 1 with lead 20 inserted within passage 16 of sheath 10. Wire 14 mates into lumen 25 and the interior of conductor 22 contacts projections, such as 19, of wire 14, thereby making electrical contact. Preferably the projections, such as 19, are slightly compressed by the interior of conductor 22, so that the contact between projections 19 and the interior of conductor 22 is a firm one. As can be best seen in FIG. 3, sheath means 12 protects the point 8 of juncture between the lead end 21 and the connector 10 so that body fluids cannot enter the juncture. The sheath 12 in this embodiment insulates and protects the electrical connection means in addition to providing the function of making the physical connection.

In FIG. 3, a suture 48 has been tied about sheath 12 further compressing the sheath 12 about lead 20. A means such as suture 48 for further compressing sheath 12 about lead 20 is optional with the invention; that is the connector according to the invention would hold firmly to lead 20 even without suture 48. In fact, it has been found that since sheath 12 is sufficiently pliable to stretch under the frictional forces created when connector 10 and lead 20 are urged in opposing directions, that as more and more force in applied between connector 10 and lead 20 in order to attempt to pull them apart, sheath 12 contracts more and more, and thus attaches itself more strongly to lead 20, so that either one of the leads 30 or 20 or 12 will break before the grip of sheath 12 on lead 20 is released. Thus, providing sheath 12 is sufficiently strong to resist breaking under the normal forces exerted on connector 10, sheath 12 will firmly hold to lead 20, under any such forces. However, since the connector is generally used in medical situtations requiring the highest degree of safety, surgeons and others using the connector may desire to doubly insure the integrity of the connection by placing further means such as 48 about sheath 12.

Figure 4:
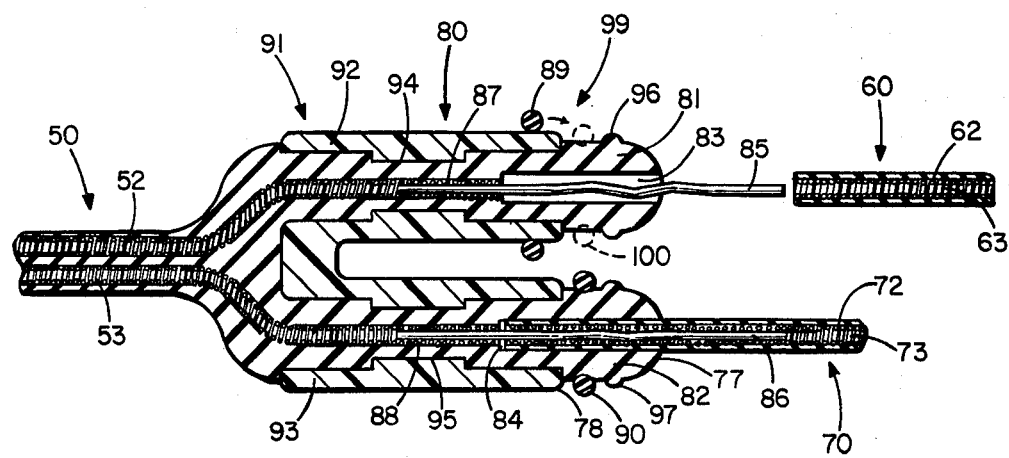
FIG. 4 is sectional view of a connector according to the invention for making connections between bipolar electrical leads and including an O-ring, the section being taken longitudinally through the axis of the leads and connector.

FIG. 4 shows another embodiment of a connector according to the invention. In this embodiment, the invention is employed to connect a bipolar lead, that is a lead in which there are two conductors. In addition, this embodiment incorporates an O-ring as a means for further compressing the sheath means about the lead. In this embodiment connector 80 is intricately formed at one end of lead 50 and is employed to connect lead 50 to a pair of leads 60 and 70. Leads 60 and 70 may be the separated portions of another bipolar lead which come together in an integral unit further to the right than the termination point of the drawing. Connector 80 comprises a pair of sheaths, 81 and 82, each having a hollow cylindrical interior passage 83 and 84. Each sheath, 81 and 82, has a wire, 85 and 86 respectively, extending longitudinally within the sheath and connected to conductors 52 and 53 of lead 50 respectively by means of welds 87 and 88 respectively. Each of leads 60 and 70 contains a conductor 62 and 72 having a lumen 63 and 73 respectively within the conductor. The connection is made by frictionally fitting sheath 81 over lead 60 and sheath 82 over lead 70 as described earlier with respect to the embodiment of FIGS. 1-3. When lead 60 is placed within sheath means 81, sheath means 81 insulates wire 85 from body fluids, while when lead 70 is placed within sheath 82, sheath 82 likewise insulates wire 85 from body fluids.

In the embodiment of FIG. 4, O-rings 89 and 90 respectively comprise the means for further compressing sheaths 81 and 82 respectively about leads 60 and 70. Connector 80 includes a means 91 for supporting O-rings 89 and 90 in a stretched condition out of contact with sheath means 81 and 82 respectively. Means 91 comprises a pair of rigid sleeves 92 and 93. Sleeve 92 encircles sheath 81 and sleeve 93 encircles sheath 82. Each of sleeves 92 and 93 include a flange 94 and 95 respectively, which prevents the sleeves from slipping off their respective sheaths. Each of sheaths 81 and 82 has a means 96 and 97 respectively for preventing the O-rings 89 and 90 respectively from slipping off the end of the sheaths. Means 96 and 97 comprise a raised portion formed in the exterior surface of the sheaths 81 and 82 respectively. Each of the raised portions 96 and 97 are located a distance from sleeves 92 and 93 respectively greater than or equal to the unstretched diameter of O-rings 89 and 90 respectively.

As can be seen best at 99, O-rings 89 and 90 may be pushed up upon sleeves 92 and 93 when they are not being used for assisting in holding their respective sheaths 81 and 82 to leads 60 and 70 respectively. After lead 60 is inserted into sheath 81, O-ring 89 may be then rolled down upon sheath 81 to further assist in holding lead 60 in place, as is shown in ghost at 100. When O-ring 89 is rolled into place on sheath 81 raised portion 96 will prevent it from rolling completely off the end of the sheath 81.

Sheaths 81 and 82 are made out of a material that is generally inert to body fluids, such as medical grade silicone rubber. By "generally inert to body fluids" it is meant that the material under normal circumstances and for a medically acceptable period of time will not react with body fluid so as to harm the body or seriously degrade the material. Sleeves 92 and 93 may be made of any material rigid enough to support an O-ring such as 89, and which is generally inert to body fluids, for example Amidel TM transparent nylon available from Union Carbide Corp. 270 Park Ave., N.Y., N.Y. The wires such as 14 and conductors such as 32 may be made out of any suitable conducting material and preferably one generally inert to body fluids such as stainless steel or platinum. The edges of the sheath such as 15 (FIG. 1) and 77 (FIG. 4) and the edges of the sleeves, such as 78 (FIG. 4) are rounded to prevent trauma to the tissues in which the connector is implanted. O-rings, such as 89, are composed of a material generally inert to body fluids, such as silicone rubber. Sutures such as 40, are made of any surgical suture material, and preferably one that is not degradable by body fluids such as silk.

It is a feature of the invention that the connector permits the length of leads within the body to be customized. The present invention permits connection with a lead to be made at any point. The length of lead necessary is determined and then the lead, such as lead 20 in FIG. 1, may be cut to the desired length. No matter where the lead is cut, the connector sheath means 12 will fit over the end of the lead, such as 21 in FIG. 1, and wire 14 will mate with lumen 25 to provide the electrical contact. This is possible because the invention requires no special fitting or other devices on the end of the lead in order to make a positive physical and electrical connection.

The connector, according to the invention, may be removed from a lead in the following manner. Referring to FIG. 3, suture 48 may be removed and the connector 10 may be grasped in one hand with the fingers projecting forward of the end 17 along the lead 20, while lead 20 is gripped with the other hand. The fingers of the first hand that are forward of the end 17 of sheath 12 may then be pulled back against end 17 compressing sheath 12. The compression of sheath 12 will cause the hollow cylindrical interior passage 16 of the sheath 12 to increase in diameter, causing it to release its grip upon lead 20. Lead 20 may then be removed from sheath 12 by a smooth steady motion, while the compression of the fingers on end 17 is maintained. The removal operation just described is more complex than the operation necessary to remove some conventional connectors, such as a socket and pin connector. However, it has been found that physicians and others using the connectors can easily learn to do the removal operation quickly. At the same time the fact that the removal operation requires a simultaneous pulling and compression action on sheath 12 while lead 20 is being pulled from the sheath, insures that conditions leading to the accidental removal of sheath 12 from lead 20 will occur only rarely, if ever. The means for further compressing the sheath, such as suture 48 and O-ring 89 additionally serve to prevent the conditions necessary for for such accidental removal.

A further feature of the invention is that the making of a connection with the connector according to the invention is very simple. Referring to FIG. 1, lead 20 only need be pushed onto wire 14 and into sheath 12. The force of lead 20 on sheath 12, which initially may be a contact force of lead tip 21A on sheath end 17 but will then quickly change to a friction force between surfaces 23 and 13 as lead end 21 enters sheath 12, will tend to compress sheath 12, thereby causing passage 16 to enlarge, permitting the passing of lead end 21 within sheath 12, until lead tip 21A abuts on the enclosed end 18 of sheath 12. Thus, a positive connection is simply and immediately made without the need for the setting of screws, the adding of adhesive, or any similar operation and it is not necessary to wait for an adhesive to set.

There has been described a novel connector that simplifies the connection of implantable electrical devices, reduces the bulk to be implanted, permits the customizing of lead length and has numerous other advantages. While the invention has been described above in connection with two particular embodiments, one skilled in the art will appreciate that the invention is not necessarily so limited and that numerous other embodiments and departures from embodiments shown may be made without departing from the inventive concepts. For example, although the invention has been described in connection with embodiments which may be connected to the end of a lead, it is contemplated that the connector according to the invention may be used to connect to many types of electrical terminals, and the end of a lead is but one type of such a terminal. Here, terminal is used in its broad sense of being any point at which energy may enter or leave a conducting element in a circuit. Further, the invention contemplates that the word "conductor" and "means for making conductive connection" be taken in their broadest sense, i.e., any type of conduction. For example, the "conductor" may be an optic fiber which conducts a light beam and the "means for making conductive connection" may be a means for conducting the light beam through the connector to the lead or other device to which the conductor connects. As another example, a suture, such as 48, may be used with a bipolar lead while an O-ring, such as 89, may be used with the unipolar lead; these aspects have been simply combined in the manner shown for purposes of illustration, and in order to not necessarily multiply the number of figures. Other equivalent electrical connectors may be used other than wire 14. The connectors, such as 10 and 80, may take on many different sizes and shapes, as may its various parts, such as sheaths 12 and 81 and sleeve 92. Additional features also may be added while employing the inventive elements.

Those skilled in the art will also see many other variations of the invention.

What is claimed is:

1. A body implantable connector for connecting to a cut end of a body implantable lead which includes a helical conductor having a lumen, the helical conductor being encased in an insulator, the connector comprising:

sheath means made of a pliable rubber-like nonconductive material which is generally insert to body fluids, the sheath means being provided with a generally cylindrical open end shaped for closely receiving a cut end of the lead and for frictionally fitting about the insulator of the lead in a generally fluid-tight connection, the material having sufficient strength to resist breaking under the forces normally exerted on the connector while implanted, but being sufficiently pliable to deform so that the sheath means contracts about the lead under the frictional forces generated between the sheath means and the insulator when the lead is urged in a direction tending to separate the lead from the connector; and a wire means mounted in the sheath means and projecting within the open end for mating in a lumen and including means for making a conductive and mechanical connection to the helical conductor.

2. The connector of claim 1 further including a member, composed of pliable material, integrally formed within the sheath means for mounting the wire means at a position to mate with the lumen.

3. The connector of claim 2 wherein the wire means has a bent portion lying at an angle to a longitudinal axis of an unbent portion of the wire means.

4. The connector to claim 3 wherein the bent portion includes a multiple bend which forms an S-shaped figuration.

5. The connector of claim 1 further comprising means for compressing the sheath means about the leads after the leads are placed within the opening, thereby increasing frictional contact between the pliable material of the sheath means and the insulator of the lead.

6. The connector of claim 5 wherein the means for compressing includes at least one resilient O-ring mounted over the sheath means.

7. The connector of claim 6 further comprising a rigid sleeve mounted over the sheath means for supporting the O-ring in a stretched condition out of contact with the sheath means while leads are being inserted in the sheath means.

8. The connector of claim 5 wherein the means for compressing includes a suture around the sheath means.

* * * * *

UNITED STATES PATENT AND TRADEMARK OFFICE
CERTIFICATE OF CORRECTION

PATENT NO. : 4,411,277
DATED : October 25, 1983
INVENTOR(S) : Eugene A. Dickhudt It is certified that error appears in the above-identified patent and that said Letters Patent are hereby corrected as shown below:

Column 2, line 63, "radical" should be --radial--;

Column 3, line 51, "portion 21 to" should be --portion 21 of--;

Column 5, line 3, "in" should be --is--;

Column 6, line 67, delete one "for"; and

Column 8, line 9, "insert" should be --inert--.

Signed and Sealed this

Tenth Day of July 1984

[SEAL]

Attest:

GERALD J. MOSSINGHOFF

Attesting Officer

Commissioner of Patents and Trademarks